United States Patent [19]

Pohndorf et al.

[11] Patent Number: 5,746,722
[45] Date of Patent: May 5, 1998

[54] SUTURE SLEEVE WITH CIRCUMFERENTIAL LEAD LOCKING DEVICE

[75] Inventors: Peter J. Pohndorf, Stillwater; Douglas H. Gubbin, Brooklyn Park, both of Minn.

[73] Assignee: Medtronic, Inc., Minneapolis, Minn.

[21] Appl. No.: 795,425

[22] Filed: Feb. 5, 1997

[51] Int. Cl.$^6$ ............................ A61N 1/04; A61M 25/04
[52] U.S. Cl. ......................... 604/175; 607/119; 604/283
[58] Field of Search ................................ 607/132, 119; 604/174, 175, 178, 179, 283

[56] References Cited

U.S. PATENT DOCUMENTS

| | | |
|---|---|---|
| 3,176,690 | 4/1965 | H'Doubler . |
| 3,724,467 | 4/1973 | Avery et al. . |
| 3,730,187 | 5/1973 | Reynolds . |
| 3,821,957 | 7/1974 | Riely et al. . |
| 3,880,169 | 4/1975 | Starr et al. . |
| 4,266,552 | 5/1981 | Dutcher et al. . |
| 4,276,882 | 7/1981 | Dickhurdt et al. . |
| 4,287,891 | 9/1981 | Peters . |
| 4,516,584 | 5/1985 | Garcia . |
| 4,553,961 | 11/1985 | Pohndorf et al. . |
| 4,672,979 | 6/1987 | Pohndorf . |
| 4,683,895 | 8/1987 | Pohndorf . |
| 4,764,132 | 8/1988 | Stutz, Jr. . |
| 4,848,346 | 7/1989 | Crawford . |
| 4,860,750 | 8/1989 | Frey et al. . |
| 4,934,366 | 6/1990 | Truex et al. . |
| 5,107,856 | 4/1992 | Kristiansen et al. . |
| 5,129,405 | 7/1992 | Milijasevic et al. . |
| 5,152,298 | 10/1992 | Kreyenhagen et al. . |
| 5,242,431 | 9/1993 | Kristiansen ............................ 604/283 |
| 5,273,053 | 12/1993 | Pohndorf . |
| 5,338,313 | 8/1994 | Mollenauer et al. ............. 604/283 |
| 5,413,595 | 5/1995 | Stutz, Jr. . |

FOREIGN PATENT DOCUMENTS 2662310  5/1991  France .

Primary Examiner—William E. Kamm
Assistant Examiner—George R. Evanisko
Attorney, Agent, or Firm—Reed A. Duthler; Harold R. Patton

[57] ABSTRACT

A suture sleeve for facilitating the ligature of an implanted catheter or lead to a patient's vein or underlying tissue having a longitudinal sleeve throughbore for receiving the lead body extending through a sleeve body and a movable locking member manually actuable between a locked and an unlocked position. The throughbore of the movable locking member is aligned with throughbores of the sleeve body, and the movable locking member and transverse channel are shaped to bias the movable locking member to the unlocked position. The locking member is movable laterally in a locking direction in a transverse channel extending laterally across the sleeve body with respect to the sleeve throughbore to a locked position that diminishes the movable locking member throughbore thereby compressing the lead body and applying a relatively uniform pressure in a band extending around its circumference, thereby minimizing lead body shear stresses. The locked position is maintained by engagement of mating fixed locking detents on the sleeve body and movable locking detents on the movable locking member. The locking member is unlocked by applying release force, preferably through the jaws of a forceps, against fixed rails on one side of the sleeve body transverse channel and against movable rails on the side of the locking member extending through the transverse channel on the other side of the sleeve body to release the locking detents and allow the locking member to move laterally in the channel to the unlocked position. When the locking member is in both the locked and the unlocked positions, the locking member throughbore is in substantial coaxial alignment with the longitudinal throughbores in the sleeve body, which are elongated in the transverse channel direction, thereby minimizing bending of the lead body in either position.

13 Claims, 4 Drawing Sheets

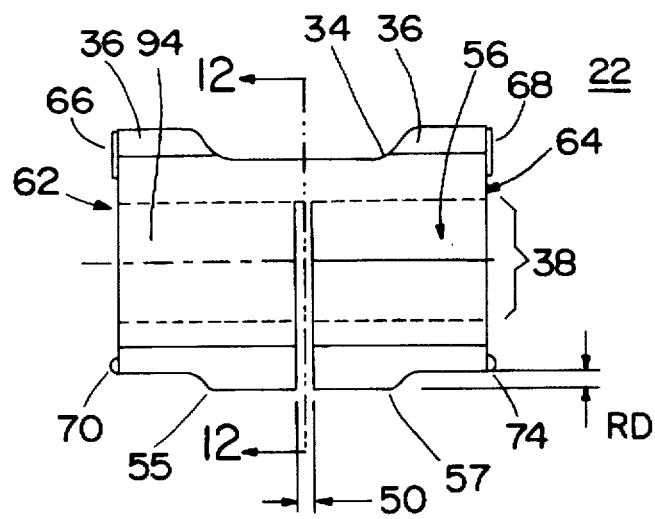
FIG.10
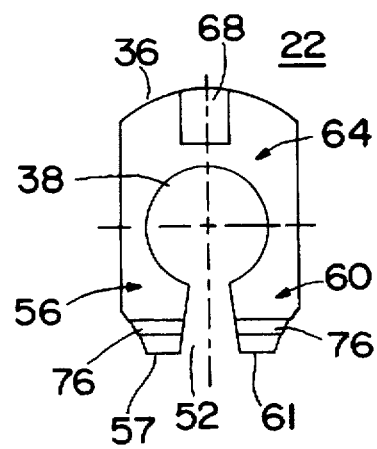
FIG.11
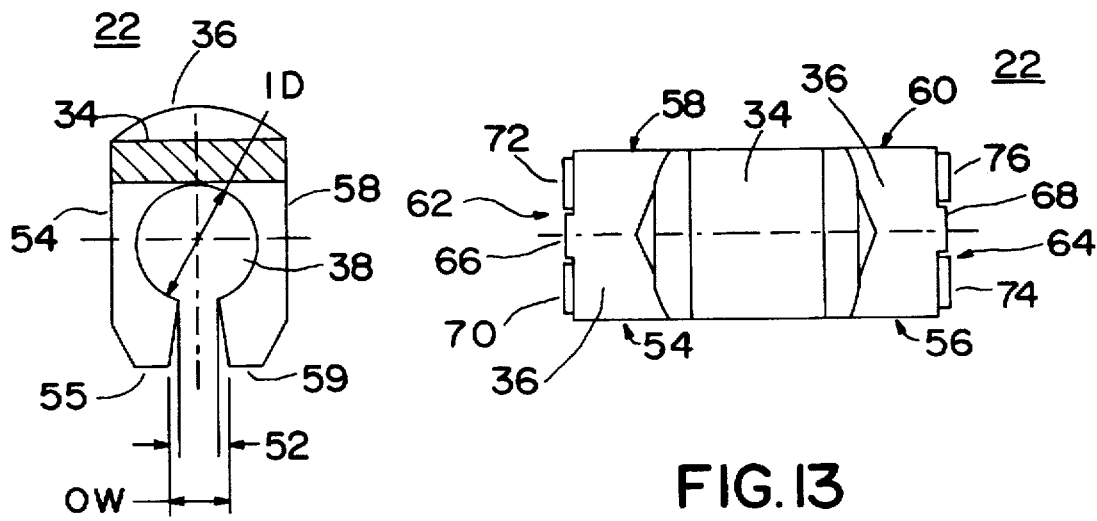
FIG.12
FIG.13
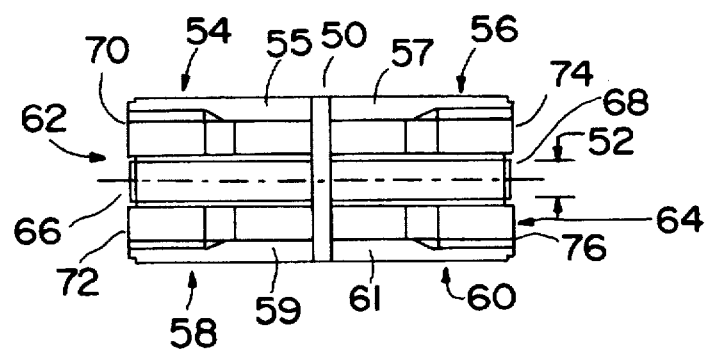
FIG.14

SUTURE SLEEVE WITH CIRCUMFERENTIAL LEAD LOCKING DEVICE

FIELD OF THE INVENTION

This invention relates to the field of implantable medical devices, and more particularly relates to suture sleeves for chronically implanted leads, catheters, and the like.

BACKGROUND OF THE INVENTION

Chronically implanted leads or catheters are used in conjunction with many different types of therapeutic implantable medical devices, such as pacemaker, cardioverter, and defibrillator pulse generators, neural stimulators, implantable drug dispensers and the like. It is generally deemed desirable to secure an implantable lead body in some manner so that proper positioning and placement of the lead is not disturbed by patient movement or migration of the pulse generator. In the past, various techniques and mechanisms have been proposed for securing implanted or partially implanted leads to body tissue in a patient as recounted in my commonly assigned U.S. Pat. No. 5,273,053.

When transvenous pacing leads became commonly used in the 1970's, physicians often employed a "butterfly-type" anchoring sleeve provided with the lead to anchor the lead to subcutaneous body tissue at or near the point where it entered the venous system. The anchoring sleeve, fitted over the lead body during implantation, provided a stable fixation point for the lead when it was sutured around the vein opening or to the adjacent subcutaneous body tissue. The butterfly-type anchoring sleeve protected the lead insulation from the stress of having a suture tied around it, as had been done in earlier times.

When polyurethane leads were introduced in the late 1970's, they were frequently provided with a pre-fitted, tubular, anchoring or suture sleeve surrounding the polyurethane lead body. These suture sleeves were typically molded of silicone rubber and were adapted to loosely fit over and slide along the lead body. In operation, the physician would slide the sleeve to a position near where the lead entered the vein and place one or more suture around it to attach it to the lead body and to the adjacent vein or body tissue to secure the lead from movement into or out of the vein. Such suture sleeves were particularly advantageous for polyurethane leads, which tended to have thinner insulation layers than earlier silicone rubber leads, and could be damaged by a suture drawn about it.

Several examples of prior art suture sleeves are known in the prior art, including those disclosed in U.S. Pat. No. 4,516,584 issued on May 14, 1985 to Garcia entitled "Suture Collar" (cylindrical collar with longitudinal bore); U.S. Pat. No. 4,553,961 issued on Nov. 19, 1985 to Pohndorf et al. entitled "Suture Sleeve with Structure for Enhancing Pacing Lead Gripping" (cylindrical collar with longitudinal bore containing structure for enhancing gripping between collar and lead); U.S. Pat. No. 4,672,979 issued on Jun. 16, 1987 to Pohndorf entitled "Suture Sleeve Assembly" (tubular sleeve and collet member adapted to snap together); U.S. Pat. No. 4,683,895 issued on Aug. 4, 1987 to Pohndorf entitled "Suture Sleeve Anchoring Device" (circular, staple-like clip for attaching a suture sleeve to tissue); U.S. Pat. No. 5,107,856 issued on Apr. 28, 1992 to Kristiansen et al. entitled "Multiple Lead Suture Sleeve" (generally "W"-shaped sleeve adapted to be compressed by sutures around one or two leads); and U.S. Pat. No. 5,129,405 issued to Milijasevic et al. on Jul. 14, 1992 entitled "Vein Suture Collar" (cylindrical collar with longitudinal bore).

Other tubular member securing mechanisms have been proposed in the prior art. Earlier examples include U.S. Pat. No. 3,176,690 issued on Apr. 6, 1965 to H'Doubler entitled "Catheter Having Integral, Polymeric Flanges" (elongated external flange integrally formed in the catheter body); U.S. Pat. No. 3,730,187 issued on May 1, 1973 to Reynolds (securing collar permanently located on the outer surface of the catheter and having a Dacron suture embedded therein); and U.S. Pat. No. 3,724,467 is-sued on Apr. 3, 1973 to Avery et al. entitled "Electrode Implant for the Neuro-Stimulation of the Spinal Cord" (physiologically inert plastic tie-down clamp); which described various types of collars or tabs attached to the tubular member for providing a suturing structure.

Still other types of lead or catheter securing devices are disclosed, for example, in U.S. Pat. No. 3,821,957 issued on Jul. 2, 1974 to Riley et al. entitled "Retention Slide for Catheters and Other Tubular Materials" (retention slide having tubular portion and four flexible, radially projecting tabs); U.S. Pat. No. 3,880,169 to Starr et al. on Apr. 29, 1975 entitled "Controlled Entry Pacemaker Electrode for Myocardial Implantation" (rectangular sewing pad adhesively bonded near distal end of lead and providing wings for suturing); U.S. Pat. No. 4,266,552 issued to Dutcher et al. on May 12, 1981 to Dutcher et al. entitled "Lead Anchoring Bobbin" (silicone rubber bobbin for receiving a looped portion of the lead); U.S. Pat. No. 4,276,882 issued on Jul. 7, 1981 to Dickhoudt et al. entitled "Lead Anchoring Device" (two-piece disc-shaped de-vice for clamping one or more leads therebetween); and U.S. Pat. No. 4,287,891 issued on Sep. 8, 1981 to Peters entitled "Securing Device" (two-piece cylindrical device with longitudinal bore which grips tubular member when twisted).

The present inventor believes that known silicone rubber suture sleeves have several disadvantages. Sleeves which must be placed on the lead during manufacture can only be removed by cutting them off, as with a scalpel, when physicians do not wish to use them. This is considered undesirable, since there is a risk that the insulation of the lead would be damaged while the sleeve was being cut off.

Moreover, it has been the inventor's experience that when a silicone rubber suture sleeve becomes wet or in-infiltrated by moisture, the friction between the lumen of the sleeve and the lead may be reduced so much that the lead is allowed to slide, and is no longer anchored in place.

In the above referenced '053 patent, a suture sleeve is provided which has a manually actuated side locking mechanism therein for securing the sleeve at any desired position along the lead body. The sleeve is formed in two parts that are fitted onto the lead body during manufacture and loosely engage one another and the lead body as long as the locking mechanism in an unlocked position. While the lead is being implanted into a patient, the physician can move the sleeve along the lead body to any desired position. Then, the physician actuates the simple push-button-type locking mechanism, causing the sleeve to be tightly secured to the lead body at the desired position. The sleeve has conventional circumferential suture grooves around it for facilitating the suturing the sleeve and lead to a vein or underlying tissue in the patent in the usual and well known manner. The locking mechanism is designed to hold the lead body securely when it is in a locked position, but yet not exert so much pressure on the lead body as to cause damage to the lead.

Although the suture sleeve of the '053 patent is designed to be simple to use, it has been determined that it is not easily unlocked without the use of a special tool other than those typically found in the operating room. Moreover, as shown in FIG. 6b of the '053 patent, the locking mechanism slightly deforms or crimps the lead body in a narrow band in a non-uniform manner, which may result in shear stresses that prove to be damaging to the lead body over a long implantation period, particularly if the stressed material tends to become brittle over time.

SUMMARY OF THE INVENTION

Accordingly, it is an object of the present invention to provide a suture sleeve for an implantable lead or catheter having a simple to use locking mechanism that can be locked manually to secure the suture sleeve at a desired point along the body of the lead or catheter and unlocked using a commonly available surgical instrument.

It is a further object of the present invention to provide a suture sleeve having such a simple locking and unlocking mechanism that exerts pressure relatively uniformly around the lead body when it is engaged in the locked position the lead body.

These and other objects of the invention are realized in a suture sleeve for facilitating suturing an implanted catheter or lead to a patient's vein or underlying tissue having a longitudinal sleeve throughbore for receiving the lead body and a manually actuated, push-button-type, locking member. The sleeve bore is defined in part by a throughbore of a movable locking member that is aligned with throughbores of a fixed sleeve body. The locking member is movable laterally in a transverse channel extending laterally across the fixed sleeve body in a locking direction with respect to the sleeve throughbore to a locked position that compresses and applies a relatively uniform pressure around the circumference of the lead body, thereby minimizing shear stresses, and engages mating locking fixed and movable locking detents.

When the locking member is in both the locked and the unlocked positions, the locking member throughbore is in substantial coaxial alignment with the longitudinal throughbores in the sleeve body. The sleeve body throughbores are elongated in the top-to-bottom direction of the transverse channel which is also the transverse direction of movement of the locking member, so that the lead body may move up or down, thereby minimizing bending of the lead body in either position. In the locked position, the locking member compresses and applies a relatively uniform pressure around the circumference of the lead body in a band, thereby also minimizing shear stresses.

The locked position is maintained by engagement of mating fixed locking detents on the sleeve body and movable locking detents on the movable locking member. The locking member is unlocked by applying opposed release forces, preferably through the jaws of a forceps, against fixed rails on one side of the sleeve body transverse channel and against movable rails on the side of the locking member extending through the transverse channel on the other side of the sleeve body to release the locking detents and allow the locking member to move laterally in the channel to the unlocked position. When the locking member is in both the locked and the unlocked positions, the locking member throughbore is in substantial coaxial alignment with the longitudinal throughbores in the sleeve body, which are elongated in the transverse channel direction, thereby minimizing bending of the lead body in either position.

BRIEF DESCRIPTION OF THE DRAWINGS

The foregoing and other aspects of the present invention will be best appreciated with reference to the detailed description of a specific embodiment of the invention, which follows, when read in conjunction with the accompanying drawings, wherein:

FIG. 10 is a side elevation view of the movable locking member of the suture sleeve;

FIG. 11 is a end view of the movable locking member of the suture sleeve;

FIG. 12 is an end cross-section view of the movable locking member of the suture sleeve;

FIG. 13 is a top view of the movable locking member of the suture sleeve; and

FIG. 14 is a bottom view of the movable locking member of the suture sleeve.

DETAILED DESCRIPTION OF A SPECIFIC EMBODIMENT OF THE INVENTION

Figure 1:
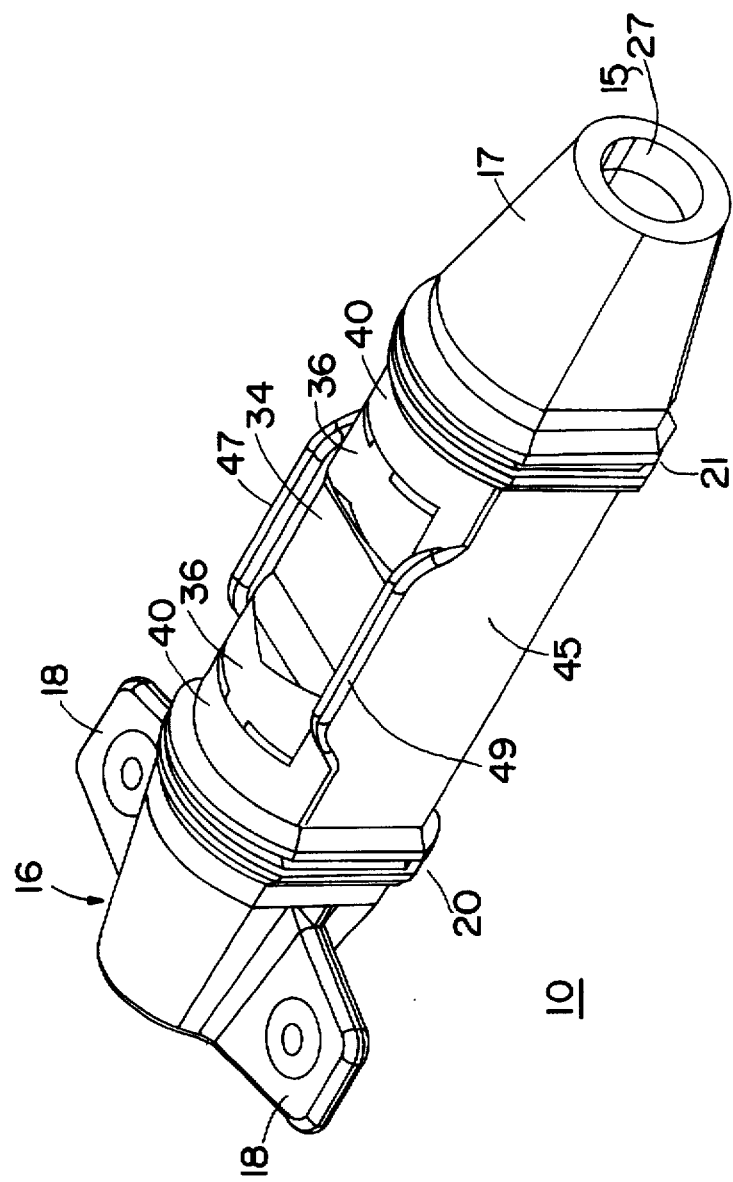
FIG. 1 is a perspective view of a suture sleeve in accordance with one embodiment of the present invention.
Figure 4:
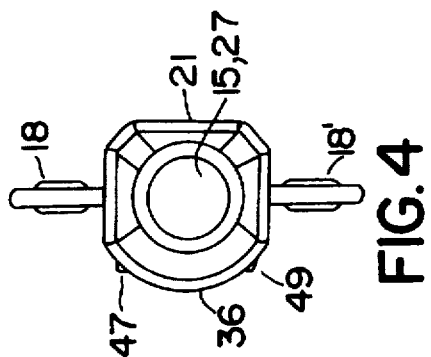
FIG. 4 is an end view of the suture sleeve depicted in FIG. 2.
Figure 5:
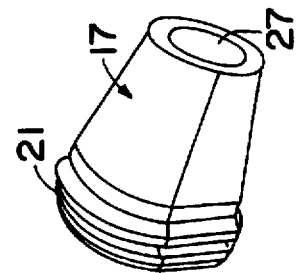
FIG. 5 is a perspective view of one of the endpieces of the suture sleeve depicted in FIGS. 1-4.
Figure 2:
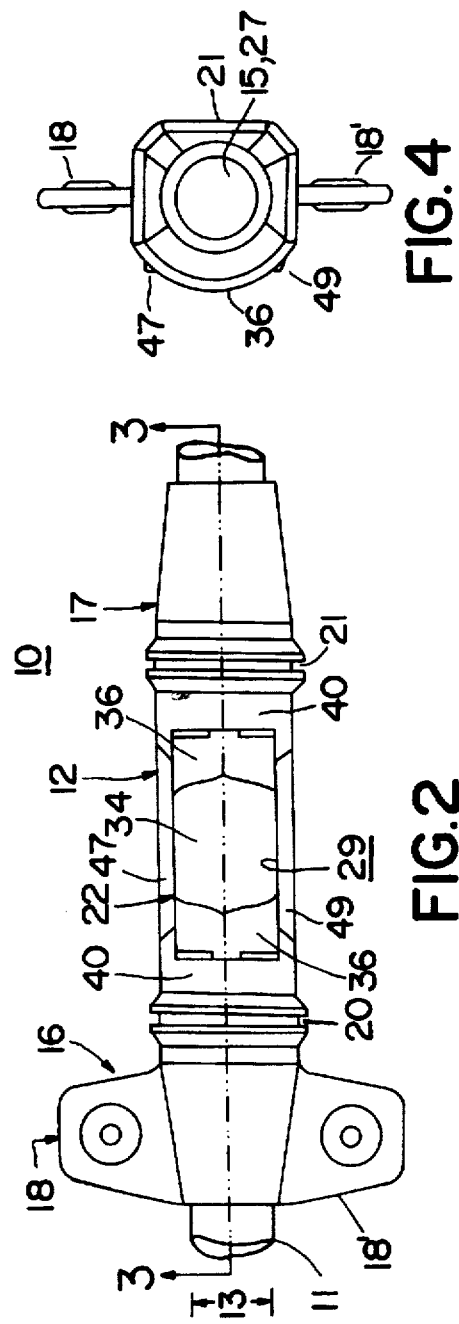
FIG. 2 is a top plan view of the suture sleeve of FIG. 1 in the locked position.

Referring to FIGS. 1 and 2, a perspective view and top plan view of an assembled suture sleeve 10 in accordance with one embodiment of the present invention are shown. It is to be understood that while suture sleeve 10 is shown in isolation in the FIG. 1 (i.e., no lead or catheter body is shown), it is contemplated that the present invention may advantageously be practiced in the context of the elongated structure, e.g. a catheter or lead body, by having a longitudinal throughbore of the suture sleeve 10 fitted onto or over the elongated, relatively cylindrical body of the implantable catheter or lead 11 (depicted in part in FIG. 2) during the manufacturing process. The lead 11 shown partly in FIG. 2 is characterized by a relatively fixed predetermined lead body diameter 13 along a predetermined length thereof intermediate its proximal and distal end structure and is formed of a resilient side wall that may be compressed. The lead body is accommodated within the longitudinal throughbore in a locked position exerting force relatively evenly around the circumference thereof or in an unlocked position allowing suture sleeve 10 to be moved along the lead body to a desired location where it may be locked in place.

The suture sleeve 10 is assembled over the lead body during manufacture of the lead 11 because implantable pacing and cardioversion leads or other leads and catheters are typically provided with relatively enlarged connectors or other structures permanently attached at their proximal ends and relatively enlarged electrodes, fixation mechanisms or the like permanently fixed at their distal ends. These enlarged proximal and distal end structures make it impractical to fit the elongated lead body into the longitudinal bore of the suture sleeve 10 after these structures are fitted to the lead body in manufacture.

Figure 3:
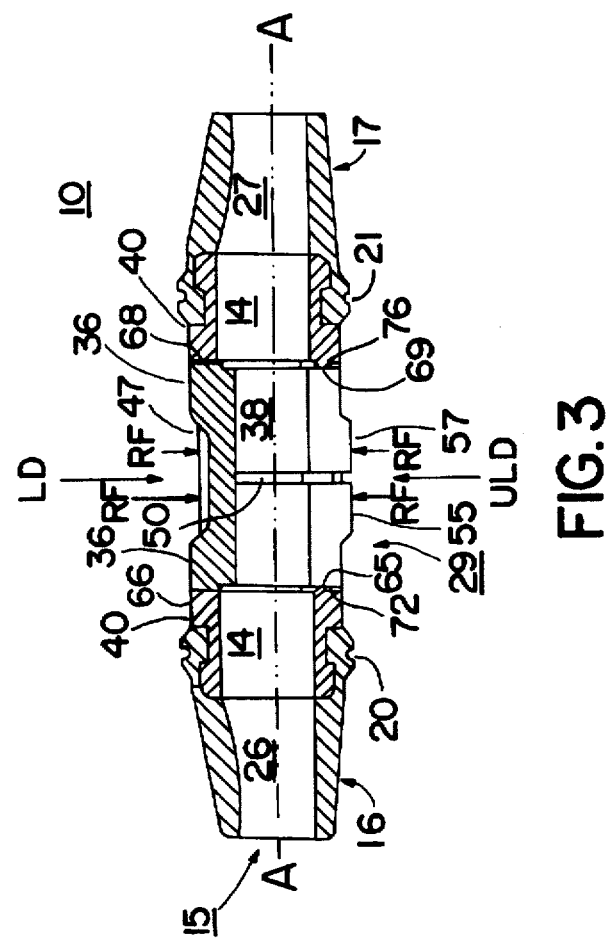
FIG. 3 is a side-cross-section view of the suture sleeve taken along section lines 3—3 in FIG. 2.
Figure 6:
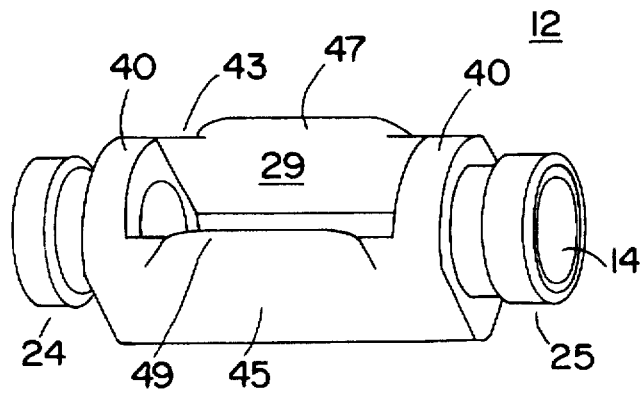
FIG. 6 is a perspective view of the fixed sleeve body of the suture sleeve.
Figure 7:
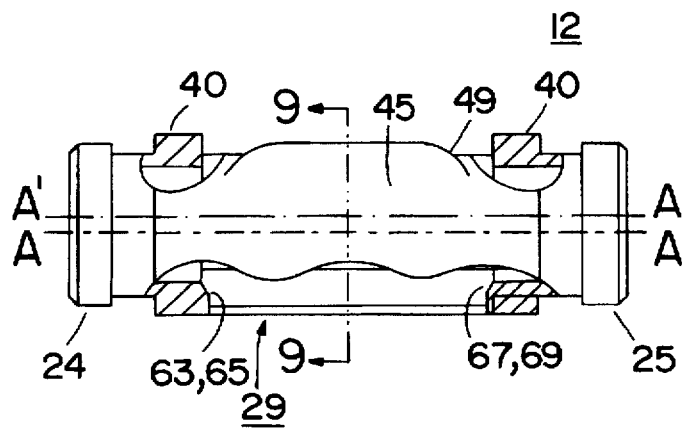
FIG. 7 is a partial side elevation view of the fixed sleeve body of the suture sleeve.

As shown in the assembly drawings of FIGS. 1 and 2 and in the side cross-section view of FIG. 3, suture sleeve 10 comprises a generally tubular sleeve body 12, endpieces 16 and 17 attached to the attachment ends 24 and 25 of sleeve body 12, and a push-button type, locking mechanism or lock member 22. Lock member 22 is positioned within a transverse channel 29 extending laterally across the sleeve body 12 from the (nominally designated) top side to the bottom side thereof. The push-button lock member 22 is movable between a locked position and an unlocked position, and is shown in the locked position in FIGS. 1–3.

Sleeve body 12 has a longitudinally extending throughbore 14 that is aligned with a throughbore 38 in the push-button lock member 22 and throughbores 26 and 27 in endpieces 16 and 17 along axial line A—A. In general, the throughbores 14, 26, 27, and 38 constitute the sleeve throughbore 15 of the assembled suture sleeve 10. In accordance with the present invention, the push-button lock member 22 may be depressed into the channel 29 in a locking direction thereby moving laterally from the unlocked position to a locked position and released from the locked position to move laterally to the unlocked position by a force applied in an unlocking direction. In the unlocked position, the diameter of the push-button lock member throughbore 38 exceeds the predetermined lead body diameter 13 and allows relative movement of the push-button lock member 22 and the sleeve body 12 and attached endpieces 16, 17 over the lead body. In the locked position, the push-button lock member throughbore diameter 38 is reduced substantially evenly about its circumference into an interference fit with the lead body diameter 13 thereby exerting force relatively evenly around the outer surface of the lead body and compressing it enough to substantially increase frictional resistance against movement of the entire suture sleeve relative to lead body.

Sleeve body 12 is generally rectangular in profile having top, bottom and side walls extending from first and second ends that are shaped with flared fittings 24 and 25 for receiving tapered endpieces 16 and 17. Sleeve body 12 is preferably formed into a relatively rigid shape by injection-molding of a relatively hard bio-compatible plastic. Endpieces 16 and 17, in the presently preferred embodiment of the invention, are made of silicone rubber or another suitably bio-compatible, relatively resilient material. Endpieces 16 and 17 are intended to serve as strain relief collars for preventing sharp and excessive bending of the lead 11 in the region of the suture sleeve, which could lead to damage to the lead and possible fatigue related failure of internal lead structures. The endpieces 16 and 17 are formed in the shape of tapered nozzles having flattened side and bottom surfaces and internal throughbores 26 and 27 that are greater in their smallest diameter than the lead body diameter 13. The fixed ends of the endpieces 16 and 17 are shaped to slip onto the flared fittings 24 and 25, respectively, as shown in FIG. 3, optionally secured by a silicone rubber based cement applied thereto.

At least endpiece 16 may optionally be provided with radially projecting fins or tabs 18, 18' for providing a suturing structure in a manner similar to that shown in prior art, for example, in the aforementioned U.S. Pat. No. 3,176,600 to H'Doubler and U.S. Pat. No. 5,107,856 to Kristiansen et al. However, it is believed by the inventor that tabs 18, 18' shown in FIG. 1 are not essential to practicing the present invention. In fact, the inventor has contemplated providing a weakened area near the points of attachment of tabs 18 to endpiece 16, so that tabs 18, 18' might be easily removed (i.e., torn, pulled, or cut off) should the implanting physician choose not to utilize them.

End pieces 16 and 17 have at least one circumferential suture groove 20 and 21, respectively, extending around its outer surface over the flared fittings 24 and 25, respectively for receiving sutures. The suture grooves 20 and 21 allow suture sleeve 10 to be sutured to a vein or underlying tissue in a conventional manner similar to that described, for example, in the aforementioned U.S. Pat. No. 5,273,053 to Pohndorf, U.S. Pat. No. 4,516,584 to Garcia, U.S. Pat. No. 4,553,961 to Pohndorf et al., U.S. Pat. No. 4,672,979 to Pohndorf, or U.S. Pat. No. 5,129,405 to Milijasevic et al. The rigidity of sleeve body 12, and in particular, the rigidity of end portions 24 and 25, prevents sutures tied around grooves 20 and 21 from being pulled so tight as to cause ligature damage to the lead body. The sutures in grooves 20, 21 function to attach suture sleeve 10 to a vein or underlying tissue in the patient, but preferably do not function to secure suture sleeve 10 to the lead body. Securing suture sleeve 10 to a lead body is instead accomplished by means of locking mechanism 22, as will become hereinafter apparent.

Turning now to FIGS. 6, 7, 8 and 9, the sleeve body 12 is depicted in perspective, side, end and end cross-section views, respectively. The axis of sleeve body throughbore 15 depicted by axial dashed line A—A (also shown in FIG. 3) extends through the end portions 24 and 25 and across the laterally extending channel 29 therebetween when the locking mechanism is in the locked position. As can be observed in FIGS. 7–9, a non-circular shape of the throughbore 14 is effected in the end portions 24 and 25 by an upward elongation of the bore by an incremental offset distance OD to form an upper axis A'—A' to accommodate the lead body in both the locked and unlocked positions of the locking member 22 as will become apparent from the following discussion. Referring back to FIG. 3, it may be observed that the aligned throughbores 26 and 27 are also elongated top to bottom by the offset distance OD to accommodate the lead body in both positions. Offset distance OD also therefore represents the amount of movement of the locking member 22 between the locked and unlocked positions.

As shown in FIGS. 6–9, the top wall 40 of the sleeve body 12 is curved, whereas the side walls 43 and 45 and bottom wall 41 are relatively flat. The laterally extending channel 29 is generally rectangular in shape at the channel opening in the top curved top wall 40 and at the channel opening in the bottom wall 41. The upper rails 47 and 49 of the side walls 43 and 45 extend above the side wall edges of the top wall channel opening in order to provide a surface against which the jaws of a forceps may be applied in the unlocking operation described below. As can be seen from FIGS. 2 and 3, in the locked position, the upper rails 47 and 49 extend above the shallow recess 34 in the locking member curved top wall 36 which itself is flush with the sleeve body 12 curved top wall 40.

The width $W_b$ of the channel opening in the bottom wall 41 is narrower than the width $W_t$ in the top wall 40 caused by the inwardly projecting lower sections of the side walls 43 and 45. As will be shown below, the lower sections of the side walls of the push-button locking member 22 are capable of being forced toward one another as they bear against the tapered inner surfaces of the lower sections of the side walls 43 and 45, thereby reducing the inside diameter ID of the locking member throughbore 38. In the absence of an applied locking force, the locking member throughbore 38 is centered at the offset A', and the lead body diameter 13 is accommodated loosely within the aligned sections of the sleeve throughbore 15. The lead body traversing the aligned sleeve throughbore 15 itself retains the locking mechanism 22 in the unlocked position within the transverse channel 29.

As will be explained further below, the locking mechanism 22 is also partially transversely sectioned below its top wall 36 and at the top of throughbore 38 by transverse section 50 shown in FIGS. 3, 10 and 14. This transverse section 50 allows the locking member end walls to be compressed toward one another as the locking member 22 is moved downward in the locking direction LD into the locked position and upward in the unlocking direction ULD into the unlocked position past a locking mechanism. As shown more clearly in FIGS. 6–13 and as described below, the locking mechanism includes movable locking detents extending outwardly from the end walls of the locking member 22 and mating fixed locking detents extending inwardly from the end walls of the transverse channel 29 adjacent to the bottom opening thereof. The compression is sufficient so that the outwardly extending, movable locking detents in the lower edges of the locking member end walls 62 and 64 can slip over the fixed locking detents 63, 65, 67, 69 formed at the lower edges of each of the inner end walls of the transverse channel 29.

Figure 9:
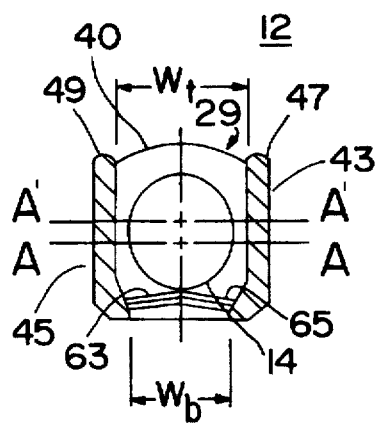
FIG. 9 is an end cross-section view of the fixed sleeve body of the suture sleeve.
Figure 8:
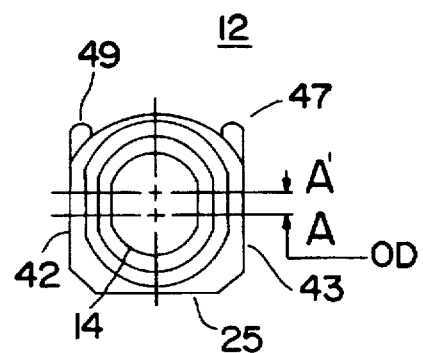
FIG. 8 is an end view of the fixed sleeve body of the suture sleeve.

Two of the fixed locking detents 63 and 65 are shown in FIG. 9, arranged at the depicted angles with respect to the plane of the lower channel opening. A like pair of fixed locking detents 67 and 69 is formed in the opposite facing end wall of the transverse channel 29. The angular arrangement allows the locking detents 63, 65 and 67, 69 to be aligned at the angles of four movable locking detents formed in four end wall sections of the locking member 22 when the sections are bent inward in the locked position as described below. The movable locking detents in the corresponding end wall sections of the locking member 22 are deflected to assume the angles of the fixed detents shown in FIG. 9 as the locking member 22 is depressed downward in the locking direction LD. The engagement of the locking detents along one side of the suture body 12 and locking member 22 is depicted in the cross-section view of FIG. 3.

Turning now to FIGS. 10–14, the push-button locking member 22 is depicted in side, top, bottom, end and end cross-section views. The locking member 22 is also preferably formed of a relatively hard, bio-compatible plastic material of the same type as the sleeve body 12. The locking member 22 is partially sectioned into four sections 54, 56, 58, 60 each having a free end extending downward from common end walls 62 and 64 by the transverse section 50 through the side walls and a further longitudinal section 52 in the bottom wall extending to the throughbore 38. The four sections 54, 56, 58, 60 are bridged together by the top wall 36 extending between end walls 62 and 64 and having the depression 34 formed in its upper surface 36. The exterior surfaces of the side walls of the four sections 54, 56, 58, 60 are relatively flat and parallel to one another and dimensioned to slide within the interior channel surfaces of sleeve body side walls 43 and 45. Chamfered lower sections of the side walls of each section are angled inward to bear against the inwardly directed lower sections of the sleeve body side walls 43 and 45.

In the unlocked and unrestrained position, the longitudinal section 52 is defined by inwardly facing inner surfaces of the four legs or sections 54, 56, 58, 60 that are angled outward to the bottom opening width OW. In the locked position, the facing inner surfaces of sections 54 and 56 are forced toward the facing inner surfaces of sections 58 and 60, respectively, reducing the opening width OW of the longitudinal section 52 and also reducing the inner diameter ID of locking member throughbore 38 substantially evenly around its circumference from the depicted unrestrained inner diameter ID. At the same time, the movable locking detents 70, 72, 74, 76 become angularly aligned with the fixed detents 63, 65, 67, 69.

The end walls 62 and 64 are relatively flat except for spacer bosses 66 and 68, respectively, extending outwardly adjacent to the top wall 36 that center the locking member 22 longitudinally within the channel 29 when it is in the locked position. The spacer bosses 66, 68 balance the four outwardly projecting, movable locking detents 70, 72, 74, 76 located adjacent the bottom edges of the end walls 62 and 64, i.e., adjacent the free ends of the four sections 54, 56, 58, 60, respectively, in the end wall surfaces thereof. As described above, the movable locking detents 70, 72, 74, 76 ride over and engage the fixed locking detents 63, 65, 67, 69 when the sections 54 and 58 are compressed toward the sections 56 and 60, respectively, which is allowed by the transverse section 50. The locked engagement of fixed detents 72 and 76 with movable locking detents 65 and 69, respectively, is depicted in FIG. 3. Although only a single movable detent engages a single fixed locking detent in each location of the mating detents, it will be understood that the mating detents may be multiplied in number.

Finally, lower rails 55, 57, 59 and 61 are formed in the bottom edges of the four sections 54, 56, 58, 60, respectively, and are dimensioned by rail depth RD (FIG. 10) to project downward in the locked position depicted in FIG. 3 so that opposed release forces RF and RF' may be applied between them and the upper rails 47 and 49. The engagement of the movable and fixed detents is released by release forces RF applied simultaneously in the transverse locking direction LD, against the upper rails 47 and 49 (rather than against the locking member 22) and opposed release forces RF' simultaneously applied and in the transverse unlocking direction ULD against the lower rails 55, 57, 59, 61. The jaws of a forceps or a similar, readily available, pliers-like tool may be applied between the lower rails 55, 57, 59 and 61, on the one hand, and the upper rails 47 and 49 on the other hand, and squeezed together. The applied compressive release forces RF and RF' push the movable locking detents 70, 72, 74, 76 upward over the fixed locking detents 63, 65, 67, 69, respectively to effect the release and movement in the unlocking direction ULD.

The locking mechanism of the present invention securely locks the suture sleeve 10 in place with minimal compression of the lead diameter 13 in a band that extends substantially evenly around the circumference of the lead body. It is to be noted from the above description that lead body diameter 13 which is only slightly smaller than the common diameter of the throughbore 15, particularly the inner diameter ID of the movable locking member 22. Since different types of catheters and leads have different diameters, it is contemplated by the inventor that sleeve 10 in accordance with the present invention must be made in different sizes to accommodate differing lead body diameters. It is believed that a person having the benefit of this disclosure would be readily able to practice the present invention with any diameter.

Although the locking mechanism comprising the fixed and movable locking detents are depicted as elongated ridges projecting outwardly of the respective end walls of the transverse channel 29 and the end walls 62 and 64, it will be understood that they may take other forms, e.g. hooks or ridges and edges or recesses, and may take other shapes, e.g., square of circular, rather than elongated. Moreover the locking mechanism may alternatively be formed in the opposing side walls of the transverse channel 29. Such equivalent structures as will be known to those of skill in the art nevertheless shall allow the substantially even compressive force to be applied substantially all the way around the circumference of the lead body or other elongated structure in the locked position.

Such equivalent structures shall additionally allow the locking mechanism to be released by release force applied in the transverse direction against the movable locking member on one side thereof and against the suture body on the other side thereof substantially as illustrated and described above.

It should be noted that, in accordance with another aspect of the present invention, after suture sleeve 10 has been locked into a desired position on the lead body as depicted in FIG. 1, suture sleeve 10 may be unlocked, if necessary, and repositioned along the lead body. Thus, suture sleeve 10 may be repeatedly locked, unlocked, and repositioned, without difficulty and without risk of damage to the lead.

The inventor has contemplated a number of design options which are available in the practice of the present invention. For example, it is contemplated that push-button locking member 22 might be marked (as with a colored dot or other symbol) in order to assist in differentiating between the top and bottom thereof. Also, it is contemplated that some portion of suture sleeve 10 may have identifying markings to distinguish, for example, between atrial and ventricular leads, or to identify the size, type or other characteristic of the lead.

Although a specific embodiment of the invention has been described herein in some detail, it is to be understood that this has been done for the purposes of illustration only, and not for the purpose of limiting the scope of the invention as defined in the following claims. It is contemplated by the inventor that various alterations, substitutions, and modifications (including, but not limited to, those alternatives expressly noted in the foregoing description) may be made to the disclosed embodiment without departing from the spirit and scope of the invention as defined in the claims.

What is claimed is:

1. A suture sleeve adapted to secure a flexible, elongated structure having a predetermined outer diameter to a patient's body tissue, comprising:

a sleeve body having a longitudinal throughbore dimensioned to fit over and receive said outer diameter of said elongated structure allowing relative movement of said sleeve body over said elongated structure, said sleeve body having a transverse channel intersecting said longitudinal throughbore;

a locking member movable within said transverse channel between an unlocked position and a locked position and having a longitudinal lock member throughbore having a throughbore diameter dimensioned to receive said outer diameter of said elongated structure in said locked and unlocked positions;

said locking member upon being moved by an applied locking force in a locking direction moving from said unlocked position wherein its throughbore diameter exceeds the predetermined outer diameter and allows relative movement of said locking member and said sleeve body over said elongated structure to said locked position wherein said locking member throughbore diameter is reduced substantially evenly about its circumference to less than said predetermined diameter, thereby exerting force relatively evenly around the outer surface of said elongated structure within said locking member throughbore to substantially increase frictional resistance against relative movement of the suture sleeve and the elongated structure; and first and second collar pieces, each collar piece having a collar piece throughbore dimensioned to receive said elongated structure and affixed to one end of said sleeve body with the collar piece throughbore in substantial coaxial alignment with said sleeve body longitudinal throughbore, each of said collar pieces being made of a resilient material and being of a length dimension sufficient to reduce substantial bending of the elongated structure extending through the sleeve body throughbore.

2. A suture sleeve in accordance with claim 1, wherein said sleeve body comprises end sections and wherein said first and second collar pieces are fitted over said end sections of said sleeve body and are provided with at least one suture receiving groove formed therein adapted to receive a suture.

3. A suture sleeve in accordance with claim 1, wherein said transverse channel is shaped to exert compressive force on said locking member in said locked position to diminish said locking member throughbore diameter.

4. A suture sleeve adapted to secure a flexible, elongated structure having a predetermined outer diameter to a patient's body tissue, comprising:

a sleeve body having a longitudinal throughbore dimensioned to fit over and receive said outer diameter of said elongated structure allowing relative movement of said sleeve body over said elongated structure, said sleeve body having a transverse channel intersecting said longitudinal throughbore;

a locking member movable within said transverse channel between an unlocked position and a locked position and having a longitudinal lock member throughbore having a throughbore diameter dimensioned to receive said outer diameter of said elongated structure in said locked and unlocked positions;

said locking member upon being moved by an applied locking force in a locking direction moving from said unlocked position wherein its throughbore diameter exceeds the predetermined outer diameter and allows relative movement of said locking member and said sleeve body over said elongated structure to said locked position wherein said locking member throughbore diameter is reduced substantially evenly about its circumference to less than said predetermined diameter, thereby exerting force relatively evenly around the outer surface of said elongated structure within said locking member throughbore to substantially increase frictional resistance against relative movement of the suture sleeve and the elongated structure, wherein said transverse channel is shaped to exert compressive force on said locking member in said locked position to diminish said locking member throughbore diameter and wherein:

said movable locking member has opposing walls and a plurality of movable locking elements formed in said opposing walls thereof; and said transverse channel is formed with like dimensioned opposing walls and a like plurality of fixed locking elements formed therein adapted to be engaged by said plurality of movable locking elements in said locked position.

5. A suture sleeve adapted to secure a flexible, elongated structure having a predetermined outer diameter to a patient's body tissue, comprising:

a sleeve body having a longitudinal throughbore dimensioned to fit over and receive said outer diameter of said elongated structure allowing relative movement of said sleeve body over said elongated structure, said sleeve body having a transverse channel intersecting said longitudinal throughbore;

a locking member movable within said transverse channel between an unlocked position and a locked position and having a longitudinal lock member throughbore having a throughbore diameter dimensioned to receive said outer diameter of said elongated structure in said locked and unlocked positions;

said locking member upon being moved by an applied locking force in a locking direction moving from said unlocked position wherein its throughbore diameter exceeds the predetermined outer diameter and allows relative movement of said locking member and said sleeve body over said elongated structure to said locked position wherein said locking member throughbore diameter is reduced substantially evenly about its circumference to less than said predetermined diameter thereby exerting force relatively evenly around the outer surface of said elongated structure within said locking member throughbore to substantially increase frictional resistance against relative movement of the suture sleeve and the elongated structure, wherein said transverse channel is shaped to exert compressive force on said locking member in said locked position to diminish said locking member throughbore diameter; and wherein:

said transverse channel extends laterally across the longitudinal throughbore of said sleeve body and is bordered by spaced apart longitudinally extending sides and laterally extending ends having at least one fixed detent formed therein;

said locking member is formed with longitudinally extending sides and laterally extending ends and is sized to fit within said transverse channel, said laterally extending ends further comprising at least one movable locking detent disposed on at least one end of said locking member for engagement with said at least one fixed locking detent in said locking mechanism.

6. A suture sleeve adapted to secure a flexible, elongated structure having a predetermined outer diameter to a patient's body tissue, comprising:

a sleeve body having a longitudinal throughbore dimensioned to fit over and receive said outer diameter of said elongated structure allowing relative movement of said sleeve body over said elongated structure, said sleeve body having a transverse channel intersecting said longitudinal throughbore;

a locking member movable within said transverse channel between an unlocked position and a locked position and having a longitudinal lock member throughbore having a throughbore diameter dimensioned to receive said outer diameter of said elongated structure in said locked and unlocked positions;

said locking member upon being moved by an applied locking force in a locking direction moving from said unlocked position wherein its throughbore diameter exceeds the predetermined outer diameter and allows relative movement of said locking member and said sleeve body over said elongated structure to said locked position wherein said locking member throughbore diameter is reduced substantially evenly about its circumference to less than said predetermined diameter thereby exerting force relatively evenly around the outer surface of said elongated structure within said locking member throughbore to substantially increase frictional resistance against relative movement of the suture sleeve and the elongated structure, wherein said transverse channel is shaped to exert compressive force on said locking member in said locked position to diminish said locking member throughbore diameter; and wherein:

said sleeve body is formed with said transverse channel extending from said transverse channel opening formed in an upper exterior surface of said sleeve body and to a further lower channel opening in a lower exterior surface of said sleeve body and is formed with first release means located adjacent the upper transverse channel opening against which a release force may be applied when said movable locking member is in the locked position without interference therewith; and said movable locking member is formed with second release means positionable in relation to said lower transverse channel opening when said movable locking member is in said locked position against which said release force may be applied when said movable locking member is in the locked position without interference with said sleeve body.

7. A suture sleeve adapted to secure a flexible, elongated structure having a predetermined outer diameter to a patient's body tissue, comprising:

a sleeve body having a longitudinal throughbore dimensioned to fit over and receive said outer diameter of said elongated structure allowing relative movement of said sleeve body over said elongated structure said sleeve body having a transverse channel intersecting said longitudinal throughbore;

a locking member movable within said transverse channel between an unlocked position and a locked position and having a longitudinal lock member throughbore having a throughbore diameter dimensioned to receive said outer diameter of said elongated structure in said locked and unlocked positions;

said locking member upon being moved by an applied locking force in a locking direction moving from said unlocked position wherein its throughbore diameter exceeds the predetermined outer diameter and allows relative movement of said locking member and said sleeve body over said elongated structure to said locked position wherein said locking member throughbore diameter is reduced substantially evenly about its circumference to less than said predetermined diameter thereby exerting force relatively evenly around the outer surface of said elongated structure within said locking member throughbore to substantially increase frictional resistance against relative movement of the suture sleeve and the elongated structure wherein said transverse channel is shaped to exert compressive force on said locking member in said locked position to diminish said locking member throughbore diameter; and wherein:

said sleeve body is formed with upper and lower exterior surfaces and said transverse channel extending from said transverse channel opening formed in said upper exterior surface and to a further lower channel opening in said lower exterior surface and is formed with at least one upper rail adjacent the upper transverse channel opening against which a release force may be applied when said movable locking member is in the locked position; and said movable locking member is formed with an upper member surface adapted to be recessed below said upper rail in said locked position and at least one lower rail adapted to extend through said lower transverse channel opening when said movable locking member is in said locked position, whereby said release force may be applied between said upper rail and said lower rail when said movable locking member is in the locked position to effect movement of said movable locking member in an unlocking direction with respect to said sleeve body.

8. A suture sleeve adapted to secure a flexible, elongated structure having a predetermined outer diameter to a patient's body tissue, comprising:

a sleeve body having a longitudinal throughbore dimensioned to fit over and receive said outer diameter of said elongated structure allowing relative movement of said sleeve body over said elongated structure, said sleeve body having a transverse channel intersecting said longitudinal throughbore;

a locking member movable within said transverse channel between an unlocked position and a locked position and having a longitudinal lock member throughbore having a throughbore diameter dimensioned to receive said outer diameter of said elongated structure in said locked and unlocked positions;

said locking member upon being moved by an applied locking force in a locking direction moving from said unlocked position wherein its throughbore diameter exceeds the predetermined outer diameter and allows relative movement of said locking member and said sleeve body over said elongated structure to said locked position wherein said locking member throughbore diameter is reduced substantially evenly about its circumference to less than said predetermined diameter, thereby exerting force relatively evenly around the outer surface of said elongated structure within said locking member throughbore to substantially increase frictional resistance against relative movement of the suture sleeve and the elongated structure, wherein said transverse channel is shaped to exert compressive force on said locking member in said locked position to diminish said locking member throughbore diameter; and wherein:

said sleeve body is formed with upper and lower opposed exterior surfaces and said transverse channel extending from said transverse channel opening formed in said upper exterior surface and to a further lower channel opening in said lower exterior surface and is formed with first and second elongated upper rails extending alongside said upper transverse channel opening against which a release force may be applied when said movable locking member is in the locked position; and said movable locking member is formed with an upper surface shaped to be recessed below said upper rail in said locked position and first and second lower rails adapted to extend through said lower transverse channel opening when said movable locking member is in said locked position, whereby said release force may be applied between said first and second upper and lower rails when said movable locking member is in the locked position to effect movement of said movable locking member in an unlocking direction with respect to said sleeve body.

9. A suture sleeve adapted to secure a flexible, elongated structure having a predetermined outer diameter to a patient's body tissue, comprising:

a sleeve body having a longitudinal throughbore dimensioned to fit over and receive said outer diameter of said elongated structure allowing relative movement of said sleeve body over said elongated structure, said sleeve body having a transverse channel intersecting said longitudinal throughbore;

a locking member movable within said transverse channel between an unlocked position and a locked position and having a longitudinal lock member throughbore having a throughbore diameter dimensioned to receive said outer diameter of said elongated structure in said locked and unlocked positions;

said locking member upon being moved by an applied locking force in a locking direction moving from said unlocked position wherein its throughbore diameter exceeds the predetermined outer diameter and allows relative movement of said locking member and said sleeve body over said elongated structure to said locked position wherein said locking member throughbore diameter is reduced substantially evenly about its circumference to less than said predetermined diameter, thereby exerting force relatively evenly around the outer surface of said elongated structure within said locking member throughbore to substantially increase frictional resistance against relative movement of the suture sleeve and the elongated structure, wherein:

said sleeve body is formed with said transverse channel extending from said transverse channel opening formed in an upper surface of said sleeve body and to a further lower channel opening in a lower surface of said sleeve body and is formed with first release means located adjacent the upper transverse channel opening against which a release force may be applied when said movable locking member is in the locked position without interference therewith; and said movable locking member is formed with second release means positionable in relation to said lower transverse channel opening when said movable locking member is in said locked position against which said release force may be applied when said movable locking member is in the locked position without interference with said sleeve body.

10. A suture sleeve adapted to secure a flexible, elongated structure having a predetermined outer diameter to a patient's body tissue, comprising:

a sleeve body having a longitudinal throughbore dimensioned to fit over and receive said outer diameter of said elongated structure allowing relative movement of said sleeve body over said elongated structure, said sleeve body having a transverse channel intersecting said longitudinal throughbore;

a locking member movable within said transverse channel between an unlocked position and a locked position and having a longitudinal lock member throughbore having a throughbore diameter dimensioned to receive said outer diameter of said elongated structure in said locked and unlocked positions;

said locking member upon being moved by an applied locking force in a locking direction moving from said unlocked position wherein its throughbore diameter exceeds the predetermined outer diameter and allows relative movement of said locking member and said sleeve body over said elongated structure to said locked position wherein said locking member throughbore diameter is reduced substantially evenly about its circumference to less than said predetermined diameter, thereby exerting force relatively evenly around the outer surface of said elongated structure within said locking member throughbore to substantially increase frictional resistance against relative movement of the suture sleeve and the elongated structure, wherein:

said sleeve body is formed with upper and lower surfaces and said transverse channel extending from said transverse channel opening formed in said upper surface of said sleeve body and to a further lower channel opening in said lower surface of said sleeve body and is formed with at least one upper rail adjacent the upper transverse channel opening against which a release force may be applied when said movable locking member is in the locked position; and said movable locking member is formed with an upper surface adapted to be recessed below said at least one upper rail in said locked position and at least one lower rail adapted to extend through said lower transverse channel opening when said movable locking member is in said locked position, whereby said release force may be applied between said upper rail and said lower rail when said movable locking member is in the locked position to effect movement of said movable locking member in an unlocking direction with respect to said sleeve body.

11. A suture sleeve adapted to secure a flexible, elongated structure having a predetermined outer diameter to a patient's body tissue, comprising:

a sleeve body having a longitudinal throughbore dimensioned to fit over and receive said outer diameter of said elongated structure allowing relative movement of said sleeve body over said elongated structure, said sleeve body having a transverse channel intersecting said longitudinal throughbore;

a locking member movable within said transverse channel between an unlocked position and a locked position and having a longitudinal lock member throughbore having a throughbore diameter dimensioned to receive said outer diameter of said elongated structure in said locked and unlocked positions.

said locking member upon being moved by an applied locking force in a locking direction moving from said unlocked position wherein its throughbore diameter exceeds the predetermined outer diameter and allows relative movement of said locking member and said sleeve body over said elongated structure to said locked position wherein said locking member throughbore diameter is reduced substantially evenly about its circumference to less than said predetermined diameter, thereby exerting force relatively evenly around the outer surface of said elongated structure within said locking member throughbore to substantially increase frictional resistance against relative movement of the suture sleeve and the elongated structure, wherein:

said sleeve body is formed with upper and lower surfaces and said transverse channel extending from said transverse channel opening formed in said upper surface of said sleeve body and to a further lower channel opening in said lower surface of said sleeve body and is formed with first and second elongated upper rails extending alongside said upper transverse channel opening against which a release force may be applied when said movable locking member is in the locked position; and said movable locking member is formed with an upper surface shaped to be recessed below said upper rail in said locked position and first and second lower rails adapted to extend through said lower transverse channel opening when said movable locking member is in said locked position, whereby said release force may be applied between said first and second upper and lower rails when said movable locking member is in the locked position to effect movement of said movable locking member in an unlocking direction with respect to said sleeve body.

12. A suture sleeve adapted to secure a flexible, elongated structure having a predetermined outer diameter to a patient's body tissue, comprising:

a sleeve body having a longitudinal throughbore dimensioned to fit over and receive said outer diameter of said elongated structure allowing relative movement of said sleeve body over said elongated structure, said sleeve body having a transverse channel intersecting said longitudinal throughbore;

a locking member movable within said transverse channel between an unlocked position and a locked position and having a longitudinal lock member throughbore having a throughbore diameter dimensioned to receive said outer diameter of said elongated structure in said locked and unlocked positions;

said locking member upon being moved by an applied locking force in a locking direction moving from said unlocked position wherein its throughbore diameter exceeds the predetermined outer diameter and allows relative movement of said locking member and said sleeve body over said elongated structure to said locked position wherein said locking member throughbore diameter is reduced substantially evenly about its circumference to less than said predetermined diameter, thereby exerting force relatively evenly around the outer surface of said elongated structure within said locking member throughbore to substantially increase frictional resistance against relative movement of the suture sleeve and the elongated structure, wherein:

said sleeve body is formed with upper and lower surfaces and separated by generally parallel side walls, said transverse channel extending from said transverse channel opening formed in said upper surface of said sleeve body and to a lower channel opening in said lower surface of said sleeve body and is bordered by channel end walls and side walls, wherein said channel side walls are formed with inwardly projecting lower, elongated sections such that said lower channel opening is narrower in width than the width of said upper channel opening; and said movable locking member is formed with generally parallel side and end walls and upper and lower surfaces dimensioned to fit within said upper transverse channel opening and to be forced toward said lower channel opening when a locking force is applied thereto and with a longitudinally extending section therein extending through said lower surface to said locking member throughbore, thereby dividing said locking member into at least two sections extending from said upper surface thereof, such that in movement of said locking member to said locked position, said elongated sections exert compressive force against said two sections of said locking member to draw them together and diminish said locking member throughbore diameter.

13. A suture sleeve in accordance with claim 12, wherein:

said sleeve body is formed with first and second elongated upper rails extending alongside said upper transverse channel opening against which a release force may be applied when said movable locking member is in the locked position; and said movable locking member is formed with an upper surface shaped to be recessed below said upper rail in said locked position and first and second lower rails adapted to extend through said lower transverse channel opening when said movable locking member is in said locked position, whereby said release force may be applied between said first and second upper and lower rails when said movable locking member is in the locked position to effect movement of said movable locking member in an unlocking direction with respect to said sleeve body.

* * * * *